United States Patent [19]
Fischer et al.

[11] Patent Number: 5,910,320
[45] Date of Patent: Jun. 8, 1999

[54] TABLET OR CAPSULE HAVING A CONTENT OF STABLE RANITIDINE HYDROCHLORIDE FORM 1

[75] Inventors: Wilfried Fischer; Karin Klokkers, both of Holzkirchen, Germany

[73] Assignee: Hexal AG, Holzkirchen, Germany

[21] Appl. No.: 08/652,439

[22] PCT Filed: Dec. 5, 1994

[86] PCT No.: PCT/EP94/04044

§ 371 Date: Aug. 19, 1996

§ 102(e) Date: Aug. 19, 1996

[87] PCT Pub. No.: WO95/15162

PCT Pub. Date: Jun. 8, 1995

[30] Foreign Application Priority Data

Dec. 3, 1993 [DE] Germany .............................. 43 41 310

[51] Int. Cl.⁶ ....................................................... A61K 9/20
[52] U.S. Cl. .......................... 424/465; 424/464; 514/970
[58] Field of Search ..................................... 424/464, 465, 424/451, 489, 452

[56] References Cited

U.S. PATENT DOCUMENTS 5,338,871  8/1994  Ngooi et al. ............................ 549/492

*Primary Examiner*—Thurman K. Page
*Assistant Examiner*—James M. Spear
*Attorney, Agent, or Firm*—Burgess, Ryan & Wayne

[57] ABSTRACT

The invention relates to a tablet or capsule that is characterised by a powder mixture having a content of stable ranitidine hydrochloride Form 1 together with a carrier and/or diluent, and to manufacturing processes for the tablet.

3 Claims, No Drawings

TABLET OR CAPSULE HAVING A CONTENT OF STABLE RANITIDINE HYDROCHLORIDE FORM 1

This application is a 371 of PCT/EP94/04044 filed Dec. 05, 1994.

BACKGROUND OF THE INVENTION

BACKGROUND ART

From GB-B-1 565 966 ranitidine hydrochloride is known in a crystalline form that according to DE-C-3 139 134 is to be referred to an Form 1. It was not yet possible according to DE-C-3 139 134, however, to produce tablets with pure and highly crystalline ranitidine hydrochloride. That prior art provides for that purpose a new form of ranitidine hydrochloride that is said to be pure and highly crystalline and is referred to as Form 2. Form 2 can be obtained by recrystallisation of Form 1, it being possible to accelerate the recrystallisation process by adding seed crystals of Form 2.

According to DE-C-3 139 134, the X-ray diffraction spectrum of Form a is characterised inter alia by a strong band $\theta=10°$ (4.40Å) which Form 1 lacks according to Hohnjec et al. in Flory, Analytical Profiles of Drug Substances, Vol. 15, 1986, pages 549 to 550. The two forms can therefore be distinguished well from each other by means of radiography.

According to the prior art mentioned, therefore, at room temperature ranitidine hydrochloride exists as Form 2, whereas Form 1 is unstable, with the result that it changes into Form 2 in the presence of seed crystals of Form 2. It is therefore to be considered surprising that, according to the invention, tablets or capsules can be provided that are characterised by a powder mixture having a content of stable ranitidine hydrochloride Form 1 together with a carrier and/or diluent.

SUMMARY OF THE INVENTION

In the tablets or capsules according to the invention, ranitidine hydrochloride Form 1 is preferably in crystal-line form.

Preferred tablets or capsules according to the invention are those in which ranitidine hydrochloride Form 2 still cannot be detected by X-ray diffractometry at least 2 years after manufacture of the tablets or capsules.

With regard to-the availability of ranitidine hydrochloride Form 1, attention in drawn to GB-B-1 565 966 and to commercial products.

DESCRIPTION OF THE PREFERRED EMBODIMENTS

The invention is explained in detail below by means of Example.

EXAMPLE 1

| | |
|---|---|
| ranitidine hydrochloride Form 1 | 336 mg |
| Aerosil | 5 mg |
| Promojel | 15 mg |
| Emcocel | 80 mg |
| Emcanpress | 31 mg |
| corn starch | 25 mg |
| talc | 5 mg |
| magnesium stearate | 3 mg |
| Total | 500 mg |

336 mg* of ranitidine hydrochloride Form 1 correspond to 300 mg of ranitidine base.
*Translator's note: There is no unit of quantity in the German text.

The above recipe was used for direct tableting wherein, according to the size of charge chosen, multiples of the given amounts of all the constituents were thoroughly mixed in the dry state and compressed in a conventional tableting press. By X-ray diffractometry it could clearly be shown that the tablets produced did not contain any ranitidine hydrochloride Form 2.

EXAMPLES 2 TO 3

| Components | Example 2 | Example 3 |
|---|---|---|
| 1 ranitidine hydrochloride Form 1 | 336.00 mg | 336.00 mg |
| 2 Avicel 101 | 64.00 mg | |
| 3 corn starch | 4.60 mg | 86.80 mg |
| 4 Kollidon 25 | 13.00 mg | 3.20 mg |
| 5 drinking water for granulation | | |
| 6 soluble starch | 8.40 mg | |
| 7 Emcocel | 40.00 mg | 30.20 mg |
| 8 Promojel | 20.00 mg | 20.00 mg |
| 9 Kollidon Cl | | 9.80 mg |
| 10 sodium dodecyl sulfate | 1.00 mg | 1.00 mg |
| 11 magnesium stearate | 3.00 mg | 3.00 mg |
| total | 490.00 mg | 490.00 mg |

According to the size of charge chosen, a multiple of components 1 to 3 was mixed in the dry state. Components 4 and 6 were dissolved in 5, followed by granulation in a WS granulator or a Lödige granulator, drying and sieving. The resulting granules were thoroughly mixed with components 7 to 11 and compressed in a tablet press to form tablets weighing 490 mg. Once again, no ranitidine hydrochloride Form 2 could be detected by X-ray diffractometry in the tablets obtained.

EXAMPLE 4

| | |
|---|---|
| ranitidine hydrochloride Form 1 | 336 mg |
| Avicel 101 | 68 mg |
| corn starch | 14 mg |
| Kollidon 25 | 14 mg |
| Promojel | 21 mg |
| magnesium stearate | 3 mg |
| sodium lauryl sulfate | 1 mg |
| Emcocel | 43 mg |
| Total | 500 mg |

Examples 2 to 3 were re-worked using this batch, granulation again being carried out with water. In this Example, no ranitidine hydrochloride Form 2 could be detected in the tablets obtained.

The composition of the aforementioned tradenames is as follows:

Avicel 101: a mixture or microcrystalline cellulose and disodium carboxymethyl cellulose.

Aerosil: silicon dioxide.

Primojel: a mixture of sodium carboxymethyl cellulose and potato starch.

Emcocel: microcrystalline cellulose.

Emcompress: dicalcium phosphate dihydrate.

Kollidon 25 or Kollidon C1:polyvinyl pyrrolidone.

We claim:

1. A process for preparing a tablet comprised of ranitidine hydrochloride which comprises forming a powder mixture by mixing, by dry means, (a) ranitidine hydrochloride Form 1, which lacks the band $\theta=10°$ (4.40Å) in the X-ray diffraction spectrum and for which no Form 2 can be detected by X-ray diffractometry after manufacture of the tablet, and (b) a carrier and/or diluent selected from the group consisting of a mixture of microcrystalline cellulose and disodium carboxymethyl cellulose, silicon dioxide, a mixture of sodium carboxymethyl cellulose and potato starch, microcrystalline cellulose, dicalcium phosphate dihydrate, starch, talc, magnesium stearate, sodium dodecyl sulfate, and polyvinyl pyrrolidone, and wherein the ratio of carrier and/or diluent to ranitidine hydrochloride is at least 0.46:1 (w/w) and thereafter compressing the powder mixture in the dry state.

2. The tablet comprised of ranitidine hydrochloride Form 1 and a carrier and/or diluent which is prepared by the process of claim 1.

3. A tablet according to claim 2, wherein ranitidine hydrochloride Form 2 still cannot be detected in the tablet by X-ray diffractometry at least 2 years after manufacture of the tablet.

* * * * *